United States Patent [19]

Reddick

[11] Patent Number: 5,649,939

[45] Date of Patent: Jul. 22, 1997

[54] LAPAROSCOPIC SUTURE INTRODUCER

[76] Inventor: Eddie J. Reddick, 790 Church St. Ext. Ste. 380, Marietta, Ga. 30060

[21] Appl. No.: 238,572

[22] Filed: May 5, 1994

Related U.S. Application Data

[63] Continuation of Ser. No. 986,807, Dec. 8, 1992, abandoned.

[51] Int. Cl.$^6$ .................................................. A61B 17/04
[52] U.S. Cl. .................................................. 606/148
[58] Field of Search .................................. 606/139, 144, 606/145, 148, 151, 167, 184, 185, 187, 181, 146; 128/898; 604/164, 264

[56] References Cited

U.S. PATENT DOCUMENTS

| | | |
|---|---|---|
| 683,655 | 10/1901 | Mersch . |
| 1,059,631 | 4/1913 | Popovics . |
| 1,539,221 | 5/1925 | Tennant . |
| 1,867,624 | 7/1932 | Hoffman . |
| 2,496,111 | 1/1950 | Turkel . |
| 2,579,192 | 12/1951 | Kohl . |
| 2,738,790 | 3/1956 | Todt . |
| 2,811,971 | 11/1957 | Scott . |
| 3,001,522 | 9/1961 | Silverman . |
| 3,154,229 | 10/1964 | Mount . |
| 3,404,677 | 10/1968 | Springer . |
| 3,406,685 | 10/1968 | May . |
| 3,410,269 | 11/1968 | Hovick . |
| 3,716,058 | 2/1973 | Tanner, Jr. . |
| 3,774,606 | 11/1973 | Norton . |
| 3,834,599 | 9/1974 | Herr . |
| 3,871,379 | 3/1975 | Clarke . |
| 3,877,434 | 4/1975 | Ferguson . |
| 3,929,123 | 12/1975 | Jamshidi . |
| 3,964,468 | 6/1976 | Schulz . |
| 3,995,619 | 12/1976 | Glatzer . |
| 4,051,844 | 10/1977 | Chiulli . |
| 4,221,212 | 9/1980 | Miller . |
| 4,235,238 | 11/1980 | Ogiu . |
| 4,243,048 | 1/1981 | Griffin . |
| 4,340,066 | 7/1982 | Shah . |
| 4,372,302 | 2/1983 | Åkerlund . |
| 4,378,019 | 3/1983 | Yamada . |
| 4,382,444 | 5/1983 | Malmin . |

(List continued on next page.)

FOREIGN PATENT DOCUMENTS

| | | | |
|---|---|---|---|
| 2908695 | 9/1980 | Germany | 606/104 |
| 3023955 | 1/1982 | Germany | 606/184 |
| 969254 | 10/1982 | U.S.S.R. . | |
| WO90/03766 | 4/1990 | WIPO | 623/13 |

OTHER PUBLICATIONS

Arthroscopy Cheater ™ American Design Group, Inc., Product Brochure. Undated.

English Translation of KUME Russian Patent 969.254.

English Translation of Bergmann German Patent No. 2,908,695.

*Primary Examiner*—Glenn Dawson
*Attorney, Agent, or Firm*—Eddie J. Reddick

[57] ABSTRACT

A medical instrument and method which permits a suture to be introduced and removed through a single cannula which leaves only a relatively small wound. The instrument employs a trocar having an elongate member having a push button at a proximal end, a sharp point and blade at a distal end, a notch formed in the trocar a short distance proximally from said distal end and an aperture through the center of the trocar extending from an opening at the proximal end to an opening at the distal end. The trocar fits within a cannula including a hollow tube having a handle at the proximal end for gripping the cannula with two fingers. A spring keeps the notch within the cannula except when the push button is depressed. The device is used by inserting the trocar in the cannula and forcing the trocar and cannula through the body of a patient. Thereafter, a suture is inserted inside the body of the patient for ligation or retraction by feeding the suture through the aperture in the trocar. Once the suture is introduced, it is manipulated around the structure to be ligated or retracted. Then, the suture is placed in the notch of the trocar and the trocar is pulled out of the cannula, which pulls the end of the suture out of the cannula as well.

22 Claims, 2 Drawing Sheets

U.S. PATENT DOCUMENTS

| | | |
|---|---|---|
| 4,392,495 | 7/1983 | Bayers . |
| 4,396,021 | 8/1983 | Baumgartner . |
| 4,406,237 | 9/1983 | Eguchi et al. . |
| 4,440,171 | 4/1984 | Nomoto et al. . |
| 4,461,281 | 7/1984 | Carson . |
| 4,465,070 | 8/1984 | Eguchi . |
| 4,493,323 | 1/1985 | Albright et al. . |
| 4,517,965 | 5/1985 | Ellison . |
| 4,602,635 | 7/1986 | Mulhollan . |
| 4,603,560 | 8/1986 | Pietrowski . |
| 4,681,123 | 7/1987 | Valtchev ................................ 606/167 |
| 4,712,545 | 12/1987 | Honkanen . |
| 4,723,546 | 2/1988 | Zagorski . |
| 4,781,190 | 11/1988 | Lee . |
| 4,784,139 | 11/1988 | Demos . |
| 4,838,282 | 6/1989 | Strasser et al. .......................... 606/184 |
| 4,874,375 | 10/1989 | Ellison . |
| 4,957,498 | 9/1990 | Caspari . |
| 4,974,758 | 12/1990 | Wünsch ................................... 223/102 |
| 5,002,550 | 3/1991 | Li . |
| 5,015,250 | 5/1991 | Foster . |
| 5,036,860 | 8/1991 | Leigh . |
| 5,037,433 | 8/1991 | Wilk et al. ............................... 606/144 |
| 5,059,201 | 10/1991 | Asnis . |
| 5,085,661 | 2/1992 | Moss ........................................ 606/139 |
| 5,090,419 | 2/1992 | Palestrant . |
| 5,149,329 | 9/1992 | Richardson . |
| 5,281,237 | 1/1994 | Gimpelson . |
| 5,342,369 | 8/1994 | Harryman, II .......................... 606/148 |

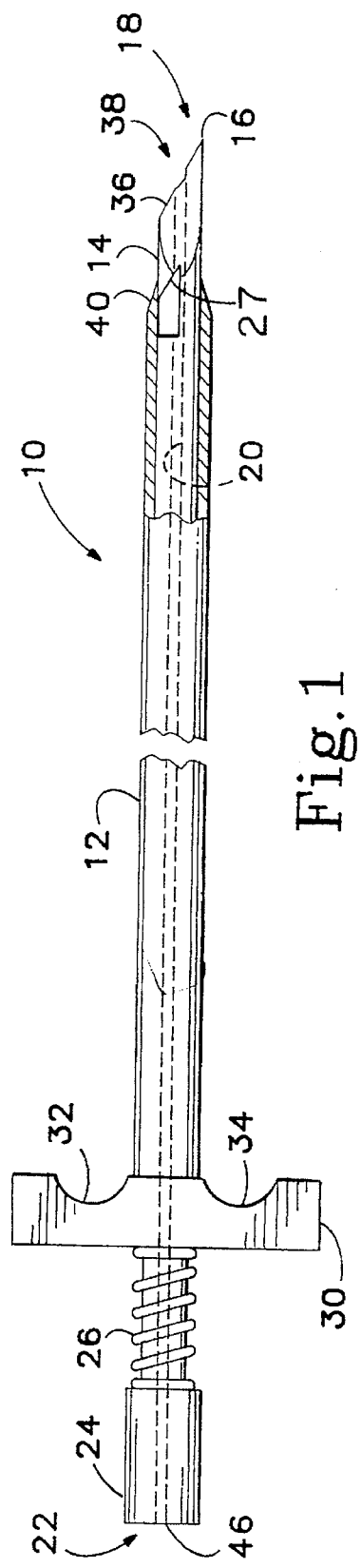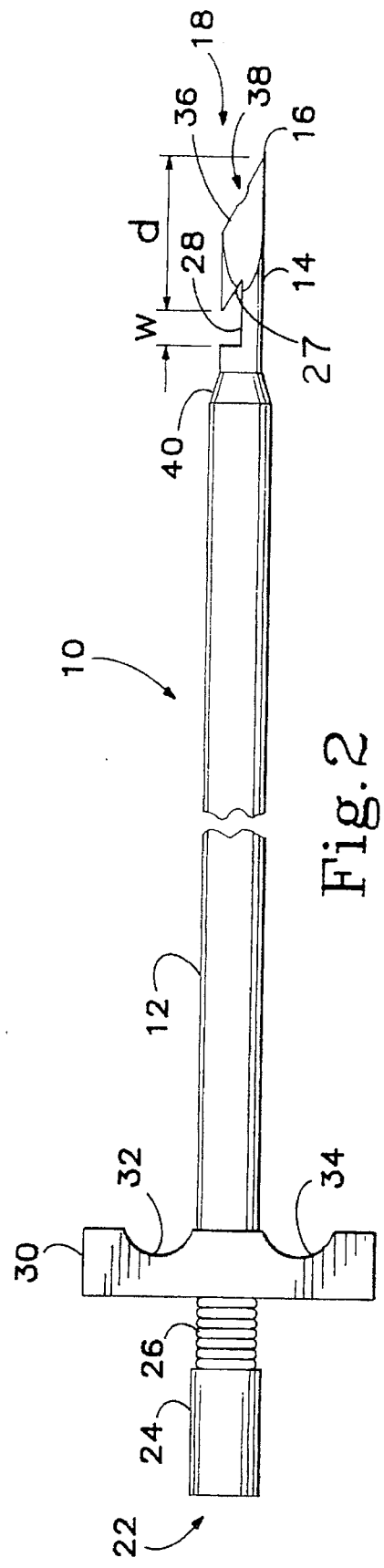

LAPAROSCOPIC SUTURE INTRODUCER

This is a continuation of application(s) Ser. No. 07/986,807 filed on Dec. 8, 1992, now abandoned.

BACKGROUND OF THE INVENTION

This invention relates to instruments and methods for performing laparoscopic surgery, particularly to instruments for introducing a suture to the inside of the body of a patient for use in ligation or retraction and methods for use thereof.

In performing laparoscopic surgery it is often desirable to use a suture to tie off, that is, ligate, a conduit such as a vessel or duct inside the body of a patient or to retract a structure inside the body of the patient. Ligation is accomplished by looping the suture around the vessel or duct, tying a slip knot with one end of the suture around the other end of the suture and cinching the knot down on the vessel or duct to close it off. Similarly, to retract a structure inside the body, the suture is looped around the structure and the ends of the suture are used to pull on the structure. Ordinarily, the suture is introduced through a cannula by attaching the suture to a needle and feeding the needle through the cannula into the body of the patient. Another surgical tool, such as a grasping forceps, introduced through another port in the body is then used to manipulate the needle inside the body of the patient. The needle is forced through the wall of the abdomen, from the inside out. Where ligation is the object, the end of the suture extending through the abdomen wall is cut inside the body of the patient, tied around the end of the suture extending out the cannula and cinched down on the duct or vessel. Where retraction is the object, the end of the suture extending out the cannula and the end of the suture extending through the wall of the abdomen are grasped and pulled to retract structure inside the body.

One problem with existing instruments and methods for ligation and retraction is that it is difficult to manipulate the needle inside the body of a person without puncturing organs or other tissue inside the body, which usually causes undesirable and dangerous complications. Another problem is that it is difficult to force the needle through the wall of the abdomen, which comprises the peritoneum, muscle, a layer of fat and the epidermis, from the inside out. A further problem is that existing instruments employ a cannula that opens about a 5 mm wound in the abdomen and the needle opens yet a further, though much smaller, wound; these wounds slow patient recovery and increase the chance that complications may occur.

Therefore, it would be desirable to have an improved instrument and method for introducing a suture to the inside of the body of a patient without the degree of trauma and difficulty experienced with conventional means for doing so.

SUMMARY OF THE INVENTION

The problems with and limitations of the aforementioned prior art devices and methods have been alleviated by the present invention through the use of a device and method which permits a suture to be introduced and removed through a single cannula which leaves only a relatively small wound. The device employs a trocar comprising an elongate member having a push button at a proximal end, a sharp point and blade at a distal end, a notch formed in the trocar a short distance proximally from said distal end and an aperture through the center of the trocar extending from an opening at the proximal end to an opening at the distal end. The trocar fits within a cannula comprising a hollow tube having a handle at the proximal end thereof. The handle comprises a laterally-disposed member having proximally-concave indentations for receiving the fingers of a user. A spring is disposed between the push button of the trocar and the handle of the cannula so that, when the trocar is disposed within the cannula, the notch in the trocar is retracted within the cannula. When the push button is depressed, the notch is moved out the end of the cannula. The distal side of the notch forms an acute angle with the bottom of the notch to facilitate grasping a suture with the trocar.

The device is used by inserting the trocar in the cannula and forcing the trocar and cannula through the body of a patient by guiding the handle of the cannula with two fingers and pressing on the push button, which incises the skin and underlying tissue of the patient, thereby allowing the cannula to be inserted therethrough. Thereafter, a suture is inserted inside the body of the patient by feeding the suture through the aperture in the trocar. Once the suture is introduced, it is manipulated around the structure to be ligated or retracted, the push button is depressed to expose the notch, the suture is placed in the notch and the push button is released to draw the suture into the cannula. The trocar is pulled out of the cannula, which pulls the end of the suture out of the cannula as well. The suture may then be used either to ligate the structure by tying a slip knot and cinching it down on the structure, or to retract the structure.

Accordingly, it is a principal object of the present invention to provide a novel and improved device and method for introducing a suture inside the body of a patient.

It is another object of the present invention to provide a novel and improved device and method for ligating a vessel or duct inside the body of a patient.

It is a further object of the present invention to provide a novel and improved device and method for retracting a structure inside the body of a patient.

It is yet another object of the present invention to provide a device and method for introducing a suture inside the body of a patient whereby both ends of the suture extend outside the body of the patient through the same port.

It is yet a further object of the present invention to provide a device and method for introducing a suture inside the body of a patient which minimizes the size and number of wounds to do so.

The foregoing and other objects, features and advantages of the invention will be more readily understood upon consideration of the following detailed description of the invention, taken in conjunction with the accompanying drawings.

BRIEF DESCRIPTION OF THE DRAWINGS

FIG. 1 shows a side view of a medical instrument according to the present invention, in partial section.

FIG. 2 shows a side view of the medical instrument of FIG. 1 with a trocar portion forced to its forward position.

DESCRIPTION OF THE PREFERRED EMBODIMENT

Figure 3:
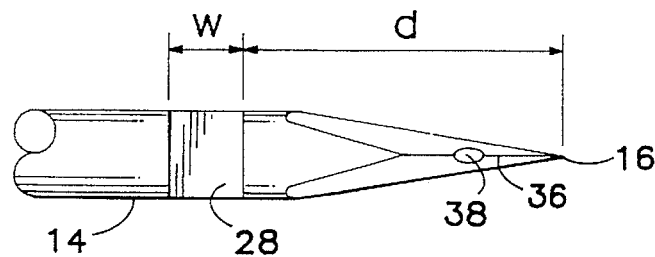
FIG. 3 shows a side view of the tip of the trocar of the medical instrument of FIGS. 1 and 2 from a side facing the cutting edge thereof.

Referring first to FIG. 1, a preferred embodiment of a medical instrument 10 according to the present invention comprises an elongate, hollow, outer shaft 12, referred to herein as a "cannula", and an inner shaft 14 referred to herein as a "trocar", disposed within the cannula 12, the trocar 14 having a sharp point 16 disposed at the distal end 18 thereof and being longitudinally movable within the cannula. The trocar includes an aperture 20 formed therein substantially throughout the entire length thereof, exiting at the distal end 18 and the proximal end 22 of the trocar 14.

An operating means is provided at the proximal end of the cannula 12 for moving the trocar 14 forward and backward. Preferably, the cannula and trocar each have cylindrical cross-sections, though it is to be recognized that other shapes could be employed without departing from the principles of the invention. The operating means comprises a push button 24 for moving the trocar 14 forward relative to the cannula, thereby activating the instrument, and a spring 26 for returning the trocar to a rearward position once the push button 24 is released. The limit of the rearward position to which the trocar 14 is returned when the instrument is not activated is determined by the length of the spring 26 when it is not compressed.

The trocar 14 is provided with a lateral notch 28 spaced a distance d proximally from the sharp point 16 of the trocar, the purpose of moving the trocar 14 forward relative to the cannula 12 being to expose the notch 28, as shown in FIG. 2. Preferably, the notch 28 has an opening of predetermined width w and a slanted distal side 27 that forms an acute angle with the bottom of the notch, as shown in FIGS. 1 and 2. The distance d and the width w of the notch are chosen so that when the push button is released, the notch is drawn entirely within the cannula 12, and when the push button 24 is fully depressed, the notch 28 is entirely exposed. The slanted side 27 of the notch facilitates grasping of a suture by the trocar, as will be explained hereafter, since the suture is forced into the intersection between the slanted side 27 and the bottom of the needle when pulling force is applied to the trocar.

In addition, a handle 30 is connected to the distal end of the cannula 12 to enable the user to grip the instrument. The handle is in the shape of an elongate, rectangular prism disposed symmetrically about the proximal end of the cannula 12. Also, the handle 30 is provided with a pair of proximally concave indentations 32 and 34, respectively, disposed on opposite sides of the cannula 12. That is, the distal side of the handle is indented in the proximal direction. These indentations permit the user to place two fingers respectively therein and the thumb of the same hand of the user on the end of the push button 24 to manipulate the instrument. By pressing down on the thumb, the trocar 14 is extended to expose the notch 28, thereby activating the instrument.

Turning to FIG. 3, as well as FIGS. 1 and 2, the sharp point 16 preferably is formed by a V-shaped cutting edge 36 extending from the distal end 18 of the trocar 14 along one side thereof rearwardly toward the proximal end of the trocar. The cutting edge may be formed by grinding the end of the trocar 14 to achieve the shape shown in FIGS. 1, 2 and 3. The aperture 20 forms a distal exit hole 38 in the cutting edge 36.

Preferably, the trocar 14 is made of a flexible metal suitable for surgical use. It should have sufficient rigidity that it will transmit adequate force from its proximal end to its distal end to cut and be pushed through the epidermis and underlying muscle of the body. The cannula 12 primarily serves as a sheath for the trocar and a pocket for the notch 28 and is preferably made of a suitable flexible material, such as plastic, so as to deform to allow a suture placed in the notch to be pulled into the cannula 12 by the trocar 14. If the cannula material is relatively thick, as may be the case where plastic is used, the cannula should preferably have a taper 40 at the distal end to facilitate forcing the instrument through the epidermis and muscle.

It is to be recognized that other materials, a different type of handle and a different type of operating means for moving the trocar 14 forward and backward may be used without departing from the principles of the invention.

Figure 4A:
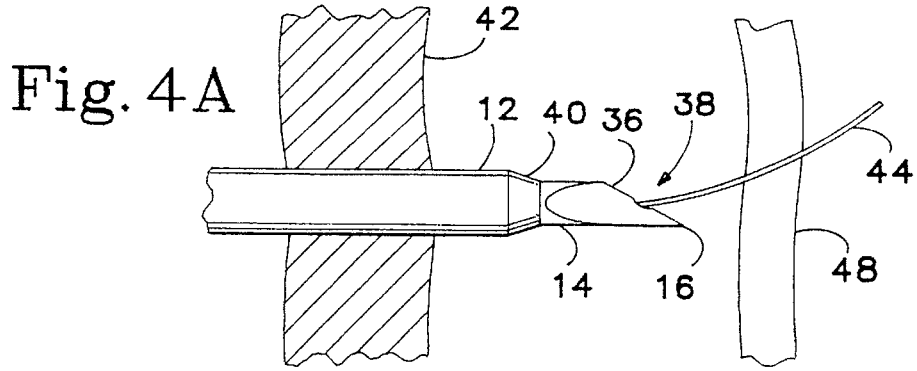
FIG. 4A shows a side view of the medical instrument of FIGS. 1, 2 and 3 inserted through the epidermis and muscle of the body of a patient, a blood vessel inside the body of the patient and a suture inserted through the medical instrument into the patient.
Figure 4B:
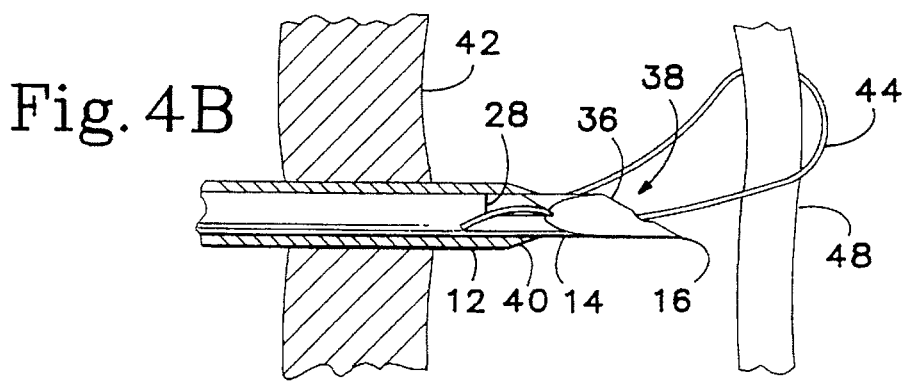
FIG. 4B shows a side view of the medical instrument of FIGS. 1, 2 and 3 inserted through the epidermis and muscle of the body of a patient, a blood vessel inside the body of the patient and a suture inserted through the medical instrument into the patient, the medical instrument being shown in partial section and the suture being shown wrapped around the blood vessel and inserted in a notch in the instrument.
Figure 4C:
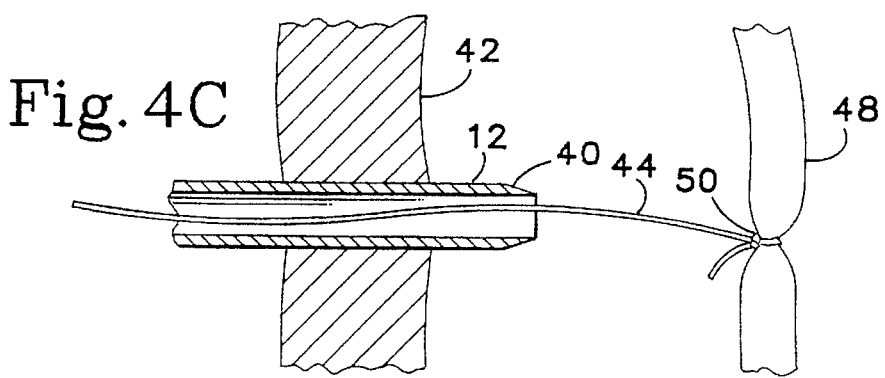
FIG. 4C shows a cannula portion of the medical instrument of FIGS. 1, 2 and 3 inserted through the epidermis and muscle of the body of a patient, with the trocar portion of the instrument removed, the suture having been tied around a blood vessel and extending out through a cannula portion of the instrument to the outside of the patient.

The method of use of the instrument 10 is illustrated in FIGS. 4A, 4B and 4C. In FIG. 4A, the instrument has been inserted through the epidermis and muscle of a patient, including any fat tissue and, in the case of the abdomen, the peritoneum as well. All of the foregoing tissues are represented by the containment member 42 in FIG. 4A. This is accomplished by the user's grasping the instrument with two fingers placed in the indentations 32 and 34 of the handle 30 and the corresponding thumb on the push button 24, and thereafter forcing the instrument through the containment member 42. The sharp point 16 of the trocar opens a small incision in the containment member, and the cutting edge 36 enlarges the incision for receipt of the cannula 12.

Once the instrument is inside the body of the patient, a suture 44 is fed through the aperture 20 by inserting it in entrance hole 46 of the trocar 14, at the proximal end of the push button 24, so as to extend out of the exit hole 38 at the distal end of the trocar, as shown in FIG. 4A. The suture may then be used to tie off, or ligate, a conduit such as a vessel or duct, or to retract a structure within the body of the patient. For example, it may be used to tie off a blood vessel 48, as shown in FIG. 4A.

Turning to FIG. 4B, once the suture 44 is inside the body, some other instrument, such as a grasping forceps introduced through another port in the body, is used to loop the suture around a structure therein, for example, the blood vessel 48, and bring the end of the suture back to the trocar 14. The trocar is extended within the cannula, as shown in FIG. 2, thereby exposing the slot 28. The end of the suture inside the body is placed in the slot 28, and the push button 24 is released, thereby pulling the trocar 14 backward in the proximal direction. This pulls the slot 28, together with the end of the suture 44, into the cannula, as shown in FIG. 4B.

Thereafter, the cannula 12 is left in place, while the trocar 14 is pulled out of the body. This leaves two ends of the suture 44 outside the body, the suture extending into the body, looping around the vessel 48 and coming back out again through the cannula.

To attach the suture 44 to tissue inside the body, or to tie off a blood vessel 48 inside the body, one end of the suture is tied in a slip knot 50 around the other end of the suture, and the other end of the suture is pulled so as to cinch the slip knot 50 around the blood vessel, thereby tying off the blood vessel. Similarly, the suture could be tightened around other structures so as to secure the suture 44 to the tissue. Thereafter, the slip knot may be tightened using other instruments inserted into the body through other ports, and the suture may be cut. Then the cannula is pulled out from the containment member 42.

To retract a structure the ends of the suture extending out of the cannula 12 can simply be used to pull on the structure.

It is to be recognized that, while the instrument and method of the present invention are preferably employed in abdominal surgery, they could also be employed for surgery of other parts of the body without departing from the principles of the invention.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A medical instrument for introducing a suture within the body of a patient, comprising:
   (a) a cannula, having a proximal end and a distal end;
   (b) a trocar, having a proximal end and a distal end and being adapted to be inserted within said cannula, said trocar terminating at the distal end thereof in a sharp point for opening an incision in tissue, having an aperture disposed substantially in the center thereof and running substantially the full length thereof so as to exit both at the distal end and adjacent the proximal end so that suture may be fed through the trocar from the proximal to the distal end;
   (c) a lateral notch in said trocar, disposed a predetermined distance proximally from said distal end; and
   (d) operating means disposed at the proximal end of said cannula for moving said trocar distally to position said notch beyond the distal end of said cannula and for moving said trocar proximally to position said notch within the distal end of said cannula.

2. The medical instrument of claim 1, wherein said operating means includes a spring connected to said cannula and to said trocar so as to apply proximally-directed force to said trocar relative to said cannula.

3. The medical instrument of claim 2, wherein said operating means includes actuation means for applying distally-directed force on said trocar relative to said cannula to overcome said proximally-directed force and move said cannula distally.

4. The medical instrument of claim 3, wherein said actuation means comprises a push button attached to the proximal end of said trocar.

5. The medical instrument of claim 4, further comprising a handle attached adjacent the proximal end of said cannula.

6. The medical instrument of claim 5, wherein said handle comprises an elongate member extending laterally on opposite sides of said cannula and substantially perpendicular thereto.

7. The medical instrument of claim 6, wherein said elongate member includes proximally-concave indentations on opposite sides of said cannula for receiving first and second fingers, respectively, of the hand of a user so that the thumb of that hand may be used to depress said push button.

8. The medical instrument of claim 1, wherein said sharp point is formed by a v-shaped cutting edge extending from a point on one side of said trocar to a position proximal therefrom on the opposite side of said trocar.

9. The medical instrument of claim 8, wherein said notch is formed in said trocar a predetermined distance proximally from said cutting edge and said notch has a predetermined length.

10. The medical instrument of claim 9, wherein said operating means includes a spring connected to said cannula and to said trocar so as to apply proximally-directed force on said trocar relative to said cannula, and actuation means for applying distally-directed force on said trocar relative to said cannula to overcome said proximally-directed force and move said cannula distally sufficiently to expose said notch.

11. The medical instrument of claim 1, further comprising a handle attached adjacent the proximal end of said cannula.

12. The medical instrument of claim 11, wherein said handle comprises an elongate member extending laterally on opposite sides of said cannula and substantially perpendicular thereto.

13. The medical instrument of claim 12, wherein said elongate member includes proximally-concave indentations on opposite sides of said cannula for receiving first and second fingers, respectively, of the hand of a user.

14. The medical instrument of claim 11, wherein said operating means includes a spring connected to said cannula and to said trocar so as to apply proximallydirected force on said trocar relative to said cannula and a push button attached to the proximal end of said trocar.

15. The medical instrument of claim 11, wherein said sharp point is formed by a v-shaped cutting edge extending from a point on one side of said trocar to a position proximal therefrom on the opposite side of said trocar.

16. The medical instrument of claim 1, wherein said operating means includes a spring connected to said cannula and to said trocar so as to apply proximally-directed force on said trocar relative to said cannula and a push button attached to the proximal end of said trocar.

17. The medical instrument of claim 1, wherein said cannula is made of a flexible material.

18. The medical instrument of claim 1, wherein said notch has a distal side that forms an acute angle with the bottom of the notch.

19. A method for introducing a suture within the body of a patient, comprising the steps of:
   (a) inserting through the epidermis and muscle of a person an instrument comprising a trocar disposed within a cannula, said trocar and cannula having respective distal and proximal ends, said trocar terminating at the distal end thereof in a sharp point and having an aperture disposed substantially in the center thereof and running substantially the full length thereof so as to exit both at the distal end and adjacent the proximal end, said trocar having a notch therein disposed a predetermined distance proximally from said distal end;
   (b) feeding a suture through said aperture within said trocar, proximate the proximal end and out the distal end thereof,
   (c) directing an end of said suture inside the body of said patient around a portion of tissue inside the body of said patient;
   (d) inserting said end of said suture into said notch; and
   (e) withdrawing said trocar from said cannula so as to pull said end of said suture outside the body of said patient.

20. The method of claim 19, further comprising the steps of tying a slip knot with said end of said suture outside the body of said patient around the other end of said suture so as to cinch said slip knot on said tissue inside the body of said patient.

21. The method of claim 20, further comprising the steps of cutting said suture adjacent said slip knot inside the body of said patient so as to leave a portion of said suture tied around said tissue inside said patient, and removing said cannula from the body of said patient.

22. The method of claim 20, wherein said tissue inside the body of said patient comprises a conduit.

* * * * *